United States Patent [19]

Crowley et al.

[11] Patent Number: 5,770,741
[45] Date of Patent: Jun. 23, 1998

[54] PROCESS FOR CYLOPROPANE DERIVATIVES

[75] Inventors: Patrick Jelf Crowley, Crowthorne; Christopher John Urch, Bracknell; Paul Anthony Worthington, Maidenhead, all of Great Britain

[73] Assignee: Sandoz Ltd., Basel, Switzerland

[21] Appl. No.: 444,663

[22] Filed: May 19, 1995

Related U.S. Application Data

[63] Continuation of Ser. No. 827,454, Jan. 29, 1992, Pat. No. 5,223,190, which is a continuation of Ser. No. 589,344, Sep. 27, 1990, abandoned, which is a division of Ser. No. 283,393, Dec. 12, 1988, Pat. No. 4,973,767.

[51] Int. Cl.$^6$ ................................................. C07D 249/08
[52] U.S. Cl. ........................................ 548/267.8; 568/322
[58] Field of Search .......................... 568/322; 548/267.8

[56] References Cited

U.S. PATENT DOCUMENTS 4,472,313  9/1984  Giger .
5,026,718  6/1991  Worthington .

FOREIGN PATENT DOCUMENTS 2129000  5/1984  United Kingdom .

Primary Examiner—Robert Gerstl
Attorney, Agent, or Firm—Lynn Marcus-Wyner; Michael P. Morris

[57] ABSTRACT

The invention provides a process for the preparation of a compound of the general formula (I):

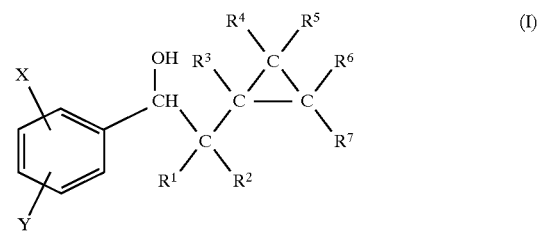

wherein X, Y and $R^1$ to $R^7$ are as defined. In the process, the olefinic analog of the compound of general formula (I) is treated with a halogen-bearing compound in the presence of metallic zinc.

6 Claims, No Drawings

PROCESS FOR CYLOPROPANE DERIVATIVES

This is a Continuation of application Ser. No. 07/827,454, filed on Jan. 29, 1992, U.S. Pat. No. 5,223,190 which is a Continuation of application Ser. No. 07/589,344, filed on Sep. 27, 1990, now abandoned, which is a Division application Ser. No. 07/283,393, filed on Dec. 12, 1988, now U.S. Pat. No. 4,973,767.

The invention described herein relates to a process for preparing certain cyclopropane derivatives useful as chemical intermediates in the preparation of agricultural products. More particularly it relates to alpha-aryl-alpha-cyclopropylalkyl-1H-azolyl ethanols including the imidazolyl and 1, 2, 4-triazolyl ethanols known to be useful as fungicides. It also relates to certain of the cyclopropane precursors themselves which are novel compounds.

Fungicidal alpha-aryl-alpha-cyclopropylalkyl-1H-azolyl ethanols are disclosed in GB-A-2136423. One process described for making them involves starting with an aryl cyclopropylalkyl methanol. Unfortunately, such compounds are not readily prepared by conventional methods.

A common method for preparing secondary and tertiary alcohols is to treat a Grignard reagent with an aldehyde or a ketone. In applying this method to the compounds of interest difficulties arise with the cyclopropylalkyl Grignard reagent. For example, 1-cyclopropylethyl bromide rearranges to the homoallylic bromide making it difficult to prepare the Grignard reagent required for the cyclopropylethyl compound. Further, it has been found that when the cyclopropylethyl Grignard reagent is reacted with an alpha-aryl-1H-1, 2, 4-triazole ethanone, the unsaturated alcohol is formed in admixture with the desired product. According to the present invention there is provided a process for the preparation of a compound of the general formula

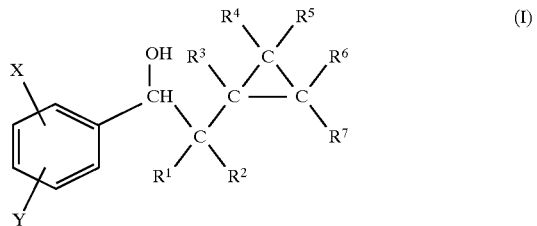

(I)

wherein X is hydrogen, halogen, alkyl, haloalkyl, cycloalkyl, cycloalkylalkyl, alkenyl, alkynyl, optionally substituted aryl, optionally substituted aralkyl, alkoxy or optionally substituted aryloxy, Y is halogen, alkyl, haloalkyl, cycloalkyl, cycloalkylalkyl, alkenyl, alkynyl, optionally substituted aryl, optionally substituted aralkyl, alkoxy or optionally substituted aryloxy, and $R^1$ to $R^7$ are independently hydrogen or $C_{1-16}$alkyl, which comprises treating a compound of the general formula (II):

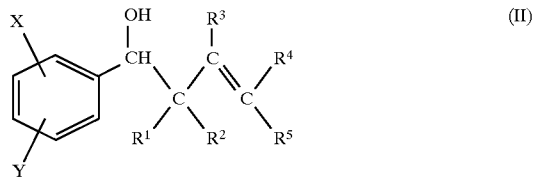

(II)

wherein X, Y and $R^1$ to $R^5$ have the meanings given before, with a compound of the general formula (III):

$CR^6R^7Z^1Z^2$ (III)

wherein $R^6$ and $R^7$ have the meanings given before, and $Z^1$ and $Z^2$, which are the same or different, are halogen in the presence of metallic zinc in an ether solvent.

Alkyl groups and the alkyl moieties of alkoxy and aralkyl groups can be in the form of straight or branched chains and contain preferably 1 to 6, more preferably 1 to 4, carbon atoms. Examples are methyls ethyl, n-propyl, n- and t-butyl and moieties thereof. Examples of haloalkyl groups are trichloro- and trifluoromethyl.

Cycloalkyl groups include $C_{3-6}$cycloalkyl and cycloalkylalkyl groups include $C_{3-6}$cycloalkyl($C_{1-4}$)alkyl. Examples are cyclopropyl, cyclohexyl and 1-cyclopropylethyl.

Alkenyl and alkynyl groups contain preferably 2 to 6, more preferably 2 to 4, carbon atoms in the form of straight or branched chains. Examples are ethenyl, allyl and propargyl.

Aryl groups and the aryl moieties of aralkyl and aryloxy groups are preferably phenyl which may be substituted with one or more of the following: halogen, $C_{1-4}$alkyl (especially methyl and ethyl), $C_{1-4}$-alkoxy (especially methoxy), haloalkyl (especially trifluoromethyl) and haloalkoxy (especially trifluoromethoxy).

Halogen, as a value of X and Y or as a substituent in any other value of X is preferably chlorine or fluorine. The halogen values of $Z^1$ and $Z^2$ are preferably selected from bromine and iodine. Usually $Z^1$ and $Z^2$ will be both bromine or both iodine.

The process of the invention is typically carried out in the presence of metallic zinc catalyst in an ether solvent under anhydrous conditions. The precise conditions will depend, inter alia, on the particular reactants involved but generally they will include those known in the literature for the Simmons-Smith reaction (see Org. React. (N.Y.), 1973, 20, 1 and J.Org.Chem., 1985, 50, 4640).

Typically, the process will be carried out in the presence of a zinc-copper couple (see J.Chem.Soc., 1978, p.1025). Zinc-silver, zinc-platinum, and zinc-palladium couples may be substituted for or used in conjunction with the zinc-copper couple (see J.Org.Chem., 1964, 29, 2049).

Other catalysts which may be employed in the process of the invention include the art-recognized nickel and cobalt complexes. Increased yields may be realized if a Lewis acid or alkali halide is used in conjunction with these catalysts. (see Chemistry Letters, 1979, pp. 761–762, Chemistry Letters, 1981, pp. 395–396, Bull.Chem.Soc.Jpn., 1983, 56, 1025–1029, and 1592–1597).

The catalyst system for the process of this invention may also comprise a zinc-based couple in the further presence of a metallo-hydride reducing agent. Suitable metallo-hydride reducing agents are described in U.S. Pat. No. 4,472,313.

While members of the general class of metallo-hydride reducing agents, may be employed, such as lithium aluminium hydride, or alkali metal borohydrides, the preferred metallic hydride reducing agents (VIII) are those which are soluble in the ether medium, and more preferably organometallic hydrides of which preferred classes include those of formula (VIIIa)

(VIIIa)

in which A signifies an alkali metal or one equivalent of an alkaline earth metal, e.g. sodium or lithium; and each of $W^1$, $W^2$ and $W^3$ is, independently, a hydrogen atom, or an alkyl or alkoxy radical of 1 to 6 arbon atoms; or an alkoxyalkoxy or alkyleneoxyalkyl radical having from 2 to 6 carbon atoms; provided that at least one of $W^1$, $W^2$ and $W^3$ is other than a hydrogen atom; or of formula (VIIIb):

in which $W^4$ and $W^5$, which may be the same or different, each signify a a hydrogen atom or an alkyl radical of 1 to 6 carbon atoms;

provided that at least one of $W_4$ and $W^5$ is alkyl.

The alkyl and alkoxy radicals mentioned above in connection with compounds of formulae (VIIIa) and (VIIIb) are understood to include as the alkyl portion thereof methyl, ethyl, propyl, butyl, amyl and hexyl, including isomers where such exist, but are preferably unbranched; and the alkylene (and alkylene portion of alkyleneoxy) radicals are understood to include methylene, ethylene, n-propylene, n-butylene, n-amylene and n-hexylene radicals, including isomers where they exist, but are preferably unbranched.

With respect to compounds of formula (VIIIa), $W^1$, $W^2$ and $W^3$ may be the same or different but are preferably the same. With respect to the compounds (VIIIb), $W^4$ and $W^5$ may be the same or different, but are preferably the same.

A suitable hydride reagent of formula (VIIIa) is sodium dihydridobis-(2-methoxyethoxy)aluminate (SDBA), which is obtainable commercially under the brand name "Vitride", and has the structure (VIIIa') NaAl[(—O—CH$_2$CH$_2$—O—CH$_3$)$_2$H$_2$] (VIIIa'), an important property of the hydride (VIIIa') is that it is soluble in a variety of solvents.

In carrying out the process it is preferred that the zinc and compound of general formula (III) each be present in molar excess, e.g. in a molar ratio of from about 2 to 6 times preferably from about 3.5 to 5 that of the compound of general formula (II). The hydride reducing agent (VIII) however, need be present only in catalytic amounts, e.g. from about 0.5% to 3%, preferably from about 1.0 to 2.0%, of the molar amount of the compound of general formula (II).

Examples of suitable solvents are diethyl ether, tetrahydrofuran dibutyl ether, dimethoxyethane, toluene, xylene, and mixtures thereof. The reaction may be facilitated by sonocation (the use of ultrasound).

The temperature at which the reaction is carried out will depend largely on the choice of solvent but it will normally be in the range of from 0° C. to 150° C., more usually from 10° C. to 100° C.

The compound of general formula (II) may be prepared by treating a compound of general formula (IV):

wherein X and Y are as previously defined, with an organometallic reagent of the general formula (V):

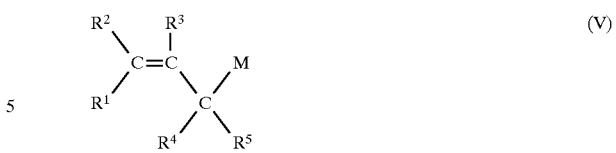

wherein $R^1$ to $R^5$ are as previously defined and M is a metal (for example, magnesium, lithium, boron, silicon, tin, chromium, aluminium or titanium). The reaction may be carried out either with or without a catalyst present using conditions described in the relevant literature for carrying out such organometallic reactions.

In particular, compounds of the general formula (II) wherein $R^1$ is hydrogen or methyl and $R^2$ to $R^5$ are hydrogen can be prepared by treating compounds of the general formula (IV) with allylmagnesium chloride or bromide, or crotylmagnesium chloride or bromide, respectively.

In another aspect, the invention includes, in combination, the process steps of:

(a) treating a compound of formula (IV) with an organometallic reagent of formula (V) to form a comound of formula (II); and (b) treating the compound of formula (II) with a compound of formula (III) to form a compound of formula (I).

Various compounds of formula I, as well as the compounds of formula (II) are believed to be novel and form yet another aspect of the present invention. Specifically, the invention includes the compounds having the formulae (Ia), (IIa) and (IIb)

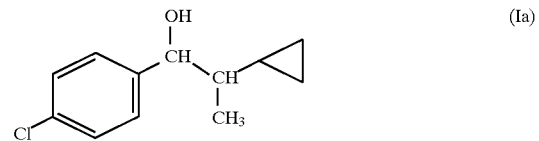

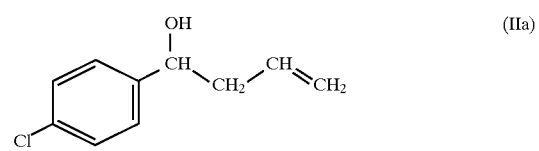

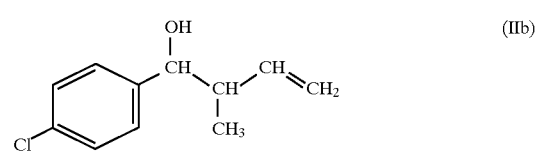

The compounds of the general formulae (IV) and (V) can be prepared by methods described in the literature.

The compounds of the general formula (I) are useful intermediates in the preparation of agricultural products of the formula (VI)

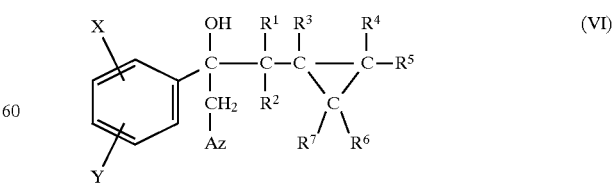

Wherein X, Y and $R^1$ to $R^7$ are as defined before, and Az is 1H-azolyl.

The products in which Az is 1H-1, 2, 4-triazolyl or 1H-imidazoyl are known to be useful as fungicides. The products of formula (VI) may be prepared in a known manner by the reaction, in the presence of a base, of the appropriate azole with an epoxide of the formula (IX)

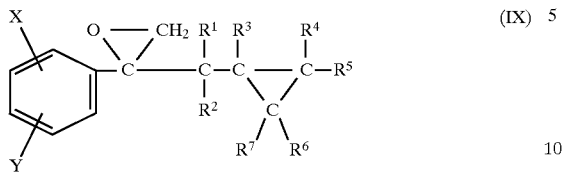

or its halohydrin derivative. The epoxide of formula (IX) and its halohydrin derivative are formed by the epoxidation of a compound of the general formula (VII):

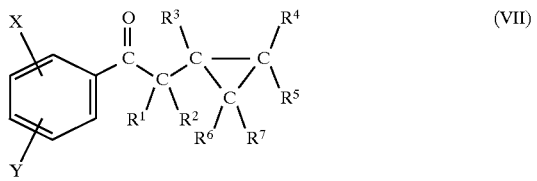

wherein X, Y and $R^1$ to $R^7$ are as previously defined.

The compounds of general formula (VII) may be obtained by oxidation of the intermediates of formula (I) using a wide variety of oxidising agents, for instance, chromium trioxide in a variety of solvents, pyridinium chlorochromate and pyridinium dichromate, or by the Moffat reaction (dimethylsulphoxide, acetic anhydride and triethylamine) or one of its variations, particularly the Swern variation (dimethylsulphoxide, oxalyl chloride and triethylamine).

In an alternative procedure, compounds of general formula (VII) wherein $R^3$ to $R^7$, X and Y are as previously defined and either one or both of $R^1$ and $R^2$ are alkyl groups, may be prepared from compounds of general formula (VIIa):

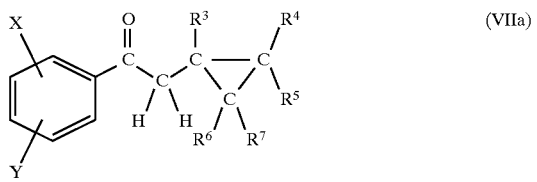

wherein $R^3$ to $R^7$ and X and Y are as previously defined, by treatment with an appropriate base and then with a compound of the formula $R^1W$ wherein $R^1$ is alkyl and W is a leaving group such as chloride, bromide, idodide, tosylate, mesylate or triflate. If $R^2$ is also alkyl the process can be repeated, treating the intermediate compound formed above first with $R^2W$, wherein $R^2$ is alkyl and W is as previously defined.

In particular, compounds of the general formula (VII), wherein $R^1$ is methyl and $R^2$ to $R^7$ are hydrogen, can be prepared by treating compounds of general formula (VII) wherein $R^1$ to $R^7$ are hydrogen with an appropriate base, for example, sodium hydride or lithium diisopropylamide and then with methyl iodide or methyl bromide at low temperature.

The compounds of formula (IX) may be obtained by reacting the compound of formula (VII) with a compound of formula (X)

wherein n is 0 or 1,

Z is halogen or methylsulfate, $R^8$ is alkyl, in the presence of a base.

In general, the procedures for preparing compounds of the formulae (VI) and (IX) from compounds of formula (VII) are known (see, e.g. U.K. Patent 2 129 000).

The invention is illustrated by the following examples in which temperatures are expressed in degrees centigrade and percentages are by weight. The term 'ether' refers to diethyl ether; chromatography was carried out using silica gel as the solid phase; and magnesium sulphate was used to dry solutions. The following abbreviations are used throughout:

| | |
|---|---|
| g = gramme(s) | s = singlet |
| mol = mole | d = doublet |
| mmol = millimole(s) | t = triplet |
| M = molar | m = multiplet |
| ml = milliliter(s) | q = quadruplet |
| IR = infrared | p = pentuplet |
| NMR = nuclear magnetic resonance | J = coupling constant |
| m/s = mass spectrograph | Hz = Hertz |
| $CDCl_3$ = deuterochloroform | $M^+$ = mass ion |

EXAMPLE 1

Preparation of 1-(4-chlorophenyl)-2-cyclopropylpropan-1-one

Crotyl chloride (154.7 g, 1.71 mol) in dry tetrahydrofuran (530 ml) was added to magnesium turnings (46.0 g, 1.89 mol) in dry tetrahydrofuran (130 ml) at such a rate so as to maintain steady reflux. After addition was complete the mixture was heated under reflux for a further hour and then cooled to 0° C. 4-Chlorobenzaldehyde (120.0 g, 0.854 mol) in dry tetrahydrofuran (780 ml) was added over a period of 2 hours. After a further hour the solution was decanted from the excess magnesium into saturated aqueous ammonium chloride solution and the magnesium washed with ether. 2 M Hydrochloric acid was added to dissolve the precipitate and the mixture extracted with ether. The combined extracts were washed with water, dried and evaporated in vacuo. Partial purification was achieved by chromatography [$SiO_2$, hexane-ethyl acetate mixtures] to give 3-methyl-4-(4-chlorophenyl)-but-1-en-4-ol (118.45 g, approximately 90% pure, approximately 64%).

3-Methyl-4-(4-chlorophenyl)but-1-en-4-ol (63.68 g, approximately 90% pure, approximately 292 mmol), dibromomethane (45.5 ml, 648 mmol), zinc dust (84.75 g, 1.296 mol) and copper(I) chloride (12.83 g, 130 mmol) in dry ether (180 ml) were heated under reflux in a sonic bath for 3½ hours. The mixture was then filtered (celite) and the filtrate poured into 2M hydrochloric acid. The mixture was extracted with ether and the combined extracts washed with water, saturated aqueous sodium bicarbonate solution and water, dried and evaporated in vacuo. Chromatography [$SiO_2$, hexane-ethyl acetate (100:0) to (80:20)] gave 1-(4-chlorophenyl)-2-cyclopropylpropan-1-ol (44.72 g, 73%).

Oxalyl chloride (22.2 ml, 255 mmol) was added to a stirred solution of dimethylsulphoxide (35 ml, 489 mmol) in dry dichloromethane (950 ml) at −78° C. under nitrogen.

After 15 minutes 1-(4-chlorophenyl)-2-cyclopropylpropan-1-ol (44.72 g, 212 mmol) in dry dichloromethane (330 ml) was added over approximately 35 minutes. After 75 minutes triethylamine (154 ml), 1105 mmol) was added and the mixture allowed to warm to room temperature. Hexane was added and the mixture washed with 1M hydrochloric acid, saturated aqueous sodium bicarbonate solution and water, dried and evaporated in vacuo. Chromatography [SiO$_2$, hexane-ethyl acetate (100:0) to (90:10)] gave 1-(4-chlorophenyl)-2-cyclopropylpropan-1-one (38.0 g, 86%).

EXAMPLE 2

Preparation of 1-(4-chlorophenyl)-2-cyclopropylpropan-1-one

Allyl chloride (97.88 g, 1.28 mol) in dry tetrahydrofuran (500 ml) was added to a suspension of magnesium turnings (60.08 g, 2.47 mol) in dry tetrahydrofuran (50 ml) at such a rate as to maintain steady reflux. The mixture was then heated under reflux for a further hour. 4-Chlorobenzaldehyde (120 g, 854 mmol) in dry tetrahydrofuran (600 ml) was then added dropwise and the mixture refluxed for a further 2 hours. After being cooled to room temperature the mixture was poured into ice/water, carefully acidified with 1M sulphuric acid and extracted with ether. The combined extracts were washed with brine, dried and evaporated in vacuo to give crude 4-(4-chlorophenyl)but-1-en-4-ol (169.4 g approximately 92% pure) which was used without further purification.

Crude 4-(4-chlorophenyl)but-1-en-4-ol from the previous reaction (85.37 g, approximately 92% pure, approximately 430 mmol), zinc dust (121.5 g, 1.86 mol), copper(I) chloride (18.69 g, 187 mmol) and dibromomethane (163.6 g, 936 mmol) in dry ether (250 ml) were heated under reflux for 3 hours in a sonic bath and then poured into 2M hydrochloric acid. The mixture was extracted with ether and the extract washed with 2M hydrochloric acid and brine, dried and evaporated in vacuo. Chromatography [SiO$_2$, hexane-ethyl acetate (90:10)] gave 1-(4-chlorophenyl)-2-cyclopropylethanol (37.24 g, 44% from 4-chlorobenzaldehyde).

Oxalyl chloride (5.5 ml, 63 mmol) was added dropwise to a stirred solution of dimethylsulphoxide (5.5 ml, 78 mmol) in dry dichloro-methane (150 ml) at −78° C. After 15 minutes 1-(4-chlorophenyl)-2-cyclopropylethanol (5.00 g, 25.4 mmol) in dry dichloromethane (60 ml) was added to the mixture. After an hour triethylamine (27.5 ml, 197 mmol) was added, the mixture warmed to room temperature and poured into water. The mixture was extracted with dichloromethane and the extracts washed with water, dried and evaporated in vacuo to give crude 1-(4-chlorophenyl)-2-cyclopropylethanone which was used without further purification.

Oxalyl chloride (14.3 ml, 160 mmol) was added dropwise to a stirred solution of dimethylsulphoxide (14.3 ml, 200 mmol) in dry dichloro-methane methane (350 ml) at −78° C. After 15 minutes 1-(4-chlorophenyl)-2-cyclopropylethanol (12.98 g, 66 mmol) in dry dichloromethane (120 ml) was added to the mixture. After an hour triethylamine (71.4 ml), 510 mmol) was added and the mixture warmed to room temperature and poured into water. The mixture was extracted with dichloromethane and the combined extracts washed with water, dried and evaporated in vacuo to give crude 1-(4-chlorophenyl)-2-cyclopropylethanone which was used without further purification.

Crude 1-(4-chlorophenyl)-2-cyclopropylethanone (from the previous reaction) in dry dimethylformamide (150 ml) was added dropwise to a stirred suspension of hexane-washed sodium hydride (4.57 g of a 60% dispersion in oil, 114 mmol) in dry dimethylformamide (35 ml) under nitrogen. After 1 hour the mixture was cooled to −30° C. and iodomethane (16.2 g, 114 mmol) in dry dimethylformamide (35 ml) added very slowly. The mixture was then poured into water and the resultant mixture extracted with ether. The extracts were washed with brine, dried and evaporated in vacuo. Chromatography [(SiO$_2$, hexane-ethyl acetate (95:5)] gave 1-(4-chlorophenyl)-2-cyclopropylpropan-1-one (7.66 g, approximately 70% pure, approximately 28% based on 1-(4-chlorophenyl)-2-cyclopropylethanol).

Spectral Data (i) 1-(4-Chlorophenyl)-2-cyclopropylpropan-1-one
IR (film): 3080, 2972, 2935, 1686, 1592, 1584, 1490, 1402, 1221, 1095, 1015, 977 and 844 cm$^{-1}$; $^1$H NMR (CDCl$_3$, 270 MHz): 7.86 (2H, m), 7.43 (2H, m), 2.74 (1H, dq, J=8.7 and 6.9 Hz), 1.28 (3H, d, J=6.9 Hz), 1.01 (1H, m), 0.54 (2H, m), and 0.18 (2H, m); m/s: 208 (15%), 141 (37), 139 (100), 111 (21), 75 (11), 69 (37) and 41 (16).

(ii) 3-Methyl-4-(4-chlorophenyl)but-1-en-4-ol)
IR (film): 3430 (broad), 3083, 2980, 2883, 1642, 1600, 1496, 1416, 1098, 1020, 924 and 828 cm$^{-1}$; $^1$H NMR (CDCl$_3$, 270 MHz): 7.40–7.15 (4H, m), 5.76 (1H, m), 5.13 (2H, m), 4.61 and 4.13 (1H, 2×d, J=5.4 and 6.9 Hz), 2.55 and 2.42 (1H, qd and p), J=6.9 and 5.4 Hz and 6.9 Hz), 2.16 and 1.94 (1H, 2×broad s) and 0.98 and 0.87 (3H, 2×d, J=6.9 and 6.9 Hz); m/s (Chemical Ionisation, ammonia): 213 (4%, M+NH$_3$) and 196 (100%, M$^+$)

(iii) 4-(4-Chlorophenyl)but-1-en-4-ol
$^1$H NMR (CDCl$_3$, 270 MHz): 7.27 (4H, m), 5.76 (1H, ddt, J=15.4, 12.3 and 6.9 Hz), 5.12 (1H, dd, J=15.4 and 2 Hz), 5.11 (1H, dd, J=12.3 and 2 Hz), 4.67 (1H, t, J=6.9 Hz), 2.89 (1H, broad s), and 2.45 (2H, t, J=6.9 Hz).

EXAMPLE 3

Preparation of 1-(4-chlorophenyl)-2-cyclopropylpropan-1-ol using SDBA catalyst

A suspension of 48 g (0.74 mol) Zn and 0.5 g (0.005 mol) Cu(I)Cl in 88 g toluene and 44 g dimethoxyethane is prepared, and maintained at 85° C. To this suspension is added 1.8 g of a 70% solution of SDBA in xylene. Thereafter is added 44 g (39.4 g at 100%=0.2 mol) of 3-methyl-4-(4-chlorophenyl) but-1-en-4-ol. Within one hour is added 101 g (0.58 mol) dibromomethane at 95° C. When the addition is completed, 0.3 g (0.003 mol) of Cu(I)Cl are added. The reaction to produce the abovetitled compound is allowed to proceed for 3 hous at 95° C. The yield is 88.1%.

What we claim is:

1. A process for preparing a compound of formula VI

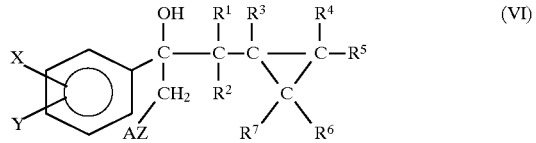

wherein X is hydrogen; halogen; C$_{1-6}$alkyl; halo(C$_{1-6}$)alkyl; C$_{3-6}$cycloalkyl; C$_{3-6}$cycloalkyl(C$_{1-4}$)alkyl; C$_{2-6}$alkenyl; C$_{2-6}$alkyny; C$_{1-6}$alkoxy: or phenyl, optionally substituted with halogen, C$_{1-4}$alkyl, C$_{1-4}$alkoxy, halo(C$_{1-4}$)alkyl, or halo(C$_{1-4}$)alkoxy;

Y is halogen; C$_{1-6}$alkyl; halo(C$_{1-6}$)alkyl; C$_{3-6}$cycloalkyl; C$_{3-6}$cycloalkyl(C$_{1-4}$)alkyl; C$_{2-6}$alkenyl; C$_{2-6}$ alkynyl; C$_{1-6}$alkoxy; or phenyl, optionally substituted with halogen, C$_{1-4}$alkyl, C$_{1-4}$alkoxy, halo(C$_{1-4}$)alkyl, or halo(C$_{1-4}$)alkoxy;

$R^1$ to $R^7$ are independently hydrogen or $C_{1-6}$alkyl; and Az is 1-H azolyl;
comprising:
a) treating a compound of formula II

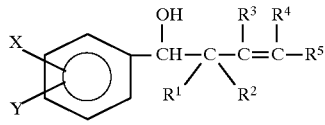

wherein X, Y, and $R^1$ to $R^5$ are as defined above, with a compound of the formula III $$CR^6R^7Z_1Z_2 \qquad (III)$$

whereas $R^6$ and $R^7$ are as defined above and $Z_2$ and $Z_2$ are the same or different and are halogen, in the presence of metallic zinc to form a compound of the formula (I)

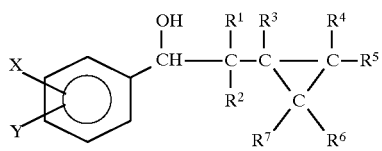

whereas X, Y, and $R^1$ and $R^7$ are as defined above;
b) oxidizing a compound of formula I in the presence of an oxidizing agent to obtain a compound of the formula (VII)

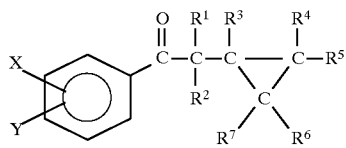

wherein X, Y, and $R^1$ to $R^7$ are as defined above;
c) epoxidizing the compound of formula VII to obtain a compound of formula (IX)

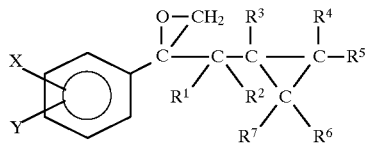

wherein X, Y, and $R^1$ to $R^7$ are as defined above; and
d) treating the compound of the formula IX with an azole to obtain the compound of the formula VI.

2. The process according to claim 1 wherein X is hydrogen and Y is halogen.

3. The process according to claim 2 wherein Y is 4-chloro, $R^1$ is methyl, $R^2$ to $R^7$ are hydgrogen and Az is 1H-1,2,4-triazolyl.

4. A process of preparing a compound of the formula VII

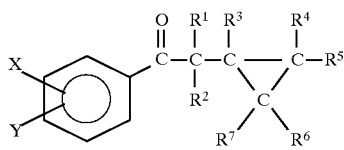

X is hydrogen; halogen; $C_{1-6}$alkyl; halo($C_{1-6}$)alkyl; $C_{3-6}$cycloalkyl; $C_{3-6}$cycloalkyl($C_{1-4}$)alkyl; $C_{2-6}$alkenyl; $C_{2-6}$alkynyl; $C_{1-6}$alkoxy; or phenyl, optionally substituted with halogen, $C_{1-4}$alkyl, $C_{1-4}$alkoxy, halo($C_{1-4}$)alkyl, or halo($C_{1-4}$)alkoxy;

Y is halogen; $C_{1-6}$alkyl; halo($C_{1-6}$)alkyl; $C_{3-6}$cycloalkyl; C3-6cycloalkyl($C_{1-4}$) alkyl; $C_{2-6}$alkenyl; $C_{2-6}$alkynyl; $C_{1-6}$alkoxy; or phenyl, optionally substituted with halogen, $C_{1-4}$alkyl, $C_{1-4}$alkoxy, halo($C_{1-4}$)alkyl, or halo($C_{1-4}$)alkoxy; and $R^1$ to $R^7$ are independently hydrogen or $C_{1-6}$alkyl;
comprising:
a) treating a compound of formula II

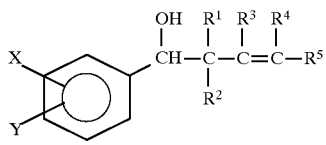

wherein X, Y, and $R^1$ to $R^5$ are defined as above, with a compound of the formula III $$CR^6R^7Z_1Z_2 \qquad (III)$$

wherein $R^6$ and $R^7$ are as defined above and $Z_1$ and $Z_2$ are the same or different and are halogen, in the presence of a metallic zinc, to form a compound of the formula I

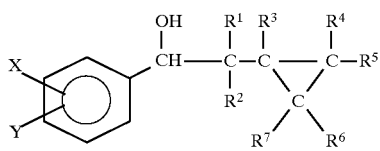

wherein X, Y and $R^1$ to $R^7$ are defined above; and
b) oxidizing in the presence of an oxidizing agent a compound of formula I.

5. A process according to claim 4 wherein X is hydgrogen and Y is halogen.

6. A process according to claim 5 wherein Y is 4-chloro, $R^1$ is methyl, and $R^2$ to $R^7$ are hydrogen.

* * * * *